(12) United States Patent
Thompson

(10) Patent No.: US 11,603,541 B2
(45) Date of Patent: Mar. 14, 2023

(54) COMPOSITIONS AND METHOD OF MAKING A COMPLEX ABLE TO INCREASE PRODUCTION OF A CETUXIMAB-LIKE PROTEIN (CLP) IN A TARGET CELL

(71) Applicant: Kinase Pharma Inc., Calgary (CA)

(72) Inventor: Bradley G. Thompson, Calgary (CA)

(73) Assignee: KINASE PHARMA INC., Calgary (CA)

( * ) Notice: Subject to any disclaimer, the term of this patent is extended or adjusted under 35 U.S.C. 154(b) by 98 days.

(21) Appl. No.: 17/313,801

(22) Filed: May 6, 2021

(65) Prior Publication Data

US 2022/0356489 A1    Nov. 10, 2022

(51) Int. Cl.
*C12N 15/86* (2006.01)
*C07K 16/28* (2006.01)
*A61K 48/00* (2006.01)

(52) U.S. Cl.
CPC .......... *C12N 15/86* (2013.01); *C07K 16/2863* (2013.01); *A61K 48/00* (2013.01); *C07K 2317/24* (2013.01); *C12N 2330/50* (2013.01); *C12N 2750/14143* (2013.01)

(58) Field of Classification Search
CPC ............... C12N 15/86; C12N 2330/50; C12N 2750/14143; C07K 16/2863; C07K 2317/24; A61K 48/00
See application file for complete search history.

(56) References Cited

U.S. PATENT DOCUMENTS 8,367,069 B2 *   2/2013  Ferris ............... A61P 37/04
                                                514/939
10,494,645 B2 * 12/2019 Auricchio ............ A61K 48/005

OTHER PUBLICATIONS

Wang D, et al. (May 2018). Nature Reviews Drug Discovery 18:358-378. (https://doi.org/10.1038/s41573-019-0012-9).*
Wilmott P, et al. (2019). Human Gene Therapy Methods 30(6):206-213. (DOI: 10.1089/hgtb.2019.276).*

* cited by examiner

*Primary Examiner* — Robert S Landsman
(74) *Attorney, Agent, or Firm* — Gowling WLG (Canada) LLP

(57) ABSTRACT

The present disclosure relates to one or more agents, therapies, treatments, and methods of use of the agents and/or therapies and/or treatments for increasing production of a Cetuximab-like protein (CLP) by a subject that is administered the agent, therapy or treatment. Embodiments of the present disclosure can be used as a therapy or a treatment for a subject that has a condition that may benefit from reducing the DNA synthesis of genes that regulate cellular growth and proliferation.

4 Claims, 1 Drawing Sheet
Specification includes a Sequence Listing.

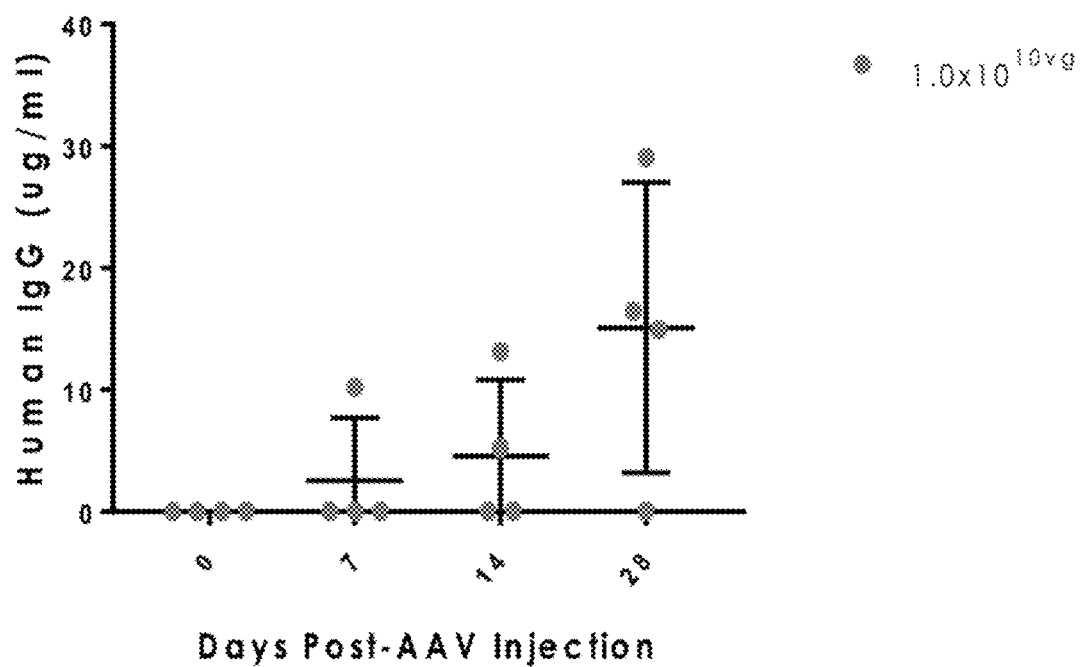

SEQUENCE LISTING

```
<160> NUMBER OF SEQ ID NOS: 9

<210> SEQ ID NO 1
<211> LENGTH: 130
<212> TYPE: DNA
<213> ORGANISM: Artificial Sequence
```

```
<220> FEATURE:
<223> OTHER INFORMATION: Synthetic Sequence

<400> SEQUENCE: 1
ctgcgcgctc gctcgctcac tgaggccgcc cgggcaaagc ccgggcgtcg ggcgaccttt      60
ggtcgcccgg cctcagtgag cgagcgagcg cgcagagagg gagtggccaa ctccatcact     120
aggggttcct                                                            130

<210> SEQ ID NO 2
<211> LENGTH: 128
<212> TYPE: DNA
<213> ORGANISM: Artificial Sequence
<220> FEATURE:
<223> OTHER INFORMATION: Synthetic Sequence

<400> SEQUENCE: 2
aggaacccct agtgatggag ttggccactc cctctctgcg cgctcgctcg ctcactgagg      60
ccgggcgacc aaaggtcgcc cgacgcccgg gctttgcccg ggcggcctca gtgagcgagc     120
gagcgcgc                                                              128

<210> SEQ ID NO 3
<211> LENGTH: 1055
<212> TYPE: DNA
<213> ORGANISM: Artificial Sequence
<220> FEATURE:
<223> OTHER INFORMATION: Synthetic Sequence

<400> SEQUENCE: 3
ggagttccgc gttacataac ttacggtaaa tggcccgcct ggctgaccgc ccaacgaccc      60
ccgcccattg acgtcaataa tgacgtatgt tcccatagta acgccaatag ggactttcca    120
ttgacgtcaa tgggtggagt atttacggta aactgcccac ttggcagtac atcaagtgta    180
tcatatgcca agtacgcccc ctattgacgt caatgacggt aaatggcccg cctggcatta    240
tgcccagtac atgaccttat gggactttcc tacttggcag tacatctacg tattagtcat    300
cgctattacc atggtcgagg tgagccccac gttctgcttc actctcccca tctccccccc    360
ctccccaccc ccaattttgt atttatttat tttttaatta ttttgtgcag cgatggggc     420 ggggggggg gggggcgcgc gccaggcggg gcggggcggg gcgaggggcg gggcggggcg    480
aggcggagag gtgcggcggc agccaatcag agcggcgcgc tccgaaagtt cctttttatg    540
gcgaggcggc ggcggcggcg gccctataaa aagcgaagcg cgcggcgggc gggagtcgct    600
gcgcgctgcc ttcgccccgt gccccgctcc gccgccgcct cgcgccgccc gccccggctc    660
tgactgaccg cgttactaaa acaggtaagt ccggcctccg cgccgggttt tggcgcctcc    720
cgcgggcgcc cccctcctca cggcgagcgc tgccacgtca gacgaagggc gcagcgagcg    780
tcctgatcct tccgcccgga cgctcaggac agcggcccgc tgctcataag actcggcctt    840
agaaccccag tatcagcaga aggacatttt aggacgggac ttgggtgact ctagggcact    900
ggttttcttt ccagagagcg gaacaggcga ggaaaagtag tcccttctcg gcgattctgc    960
ggagggatct ccgtggggcg gtgaacgccg atgatgcctc tactaaccat gttcatgttt    1020 tcttttttt tctacaggtc ctgggtgacg aacag                                1055

<210> SEQ ID NO 4
<211> LENGTH: 360
<212> TYPE: DNA
<213> ORGANISM: Artificial Sequence
<220> FEATURE:
```

<223> OTHER INFORMATION: Synthetic Sequence

<400> SEQUENCE: 4

| caggtacaac tgaaacaaag cgggcctggg ctggtccagc catcccaaag tttgtccata | 60 |
| acttgcactg ttagtggttt tagcttgacc aattacgggg tgcattgggt aagacagagt | 120 |
| cctggtaagg gcctcgaatg gctgggcgtg atatggtcag gcggcaatac tgactacaat | 180 |
| actccattta ccagcagatt gtccatcaat aaagataatt ctaaaagcca ggtattcttt | 240 |
| aagatgaact ctctgcagtc caatgatact gcaatttatt actgtgcccg agcacttacc | 300 |
| tactacgatt acgagttcgc atactggggc cagggtaccc tcgtgaccgt atctgcagcg | 360 |

<210> SEQ ID NO 5
<211> LENGTH: 324
<212> TYPE: DNA
<213> ORGANISM: Artificial Sequence
<220> FEATURE:
<223> OTHER INFORMATION: Synthetic Sequence

<400> SEQUENCE: 5

| gatatccttc tgactcaatc ccctgtgatt ctgtcagtgt caccagggga aagggtcagt | 60 |
| ttttcatgtc gcgcatctca aagcattggc actaacatcc actggtacca acaacgcaca | 120 |
| aacggaagtc cccgcttgct catcaagtat gcaagcgaat caatcagcgg gatcccttcc | 180 |
| aggttcagtg gtagtgggag tggtacagat ttcactctct caattaacag cgtagagtcc | 240 |
| gaggacatcg ccgactatta ttgccaacag aacaacaact ggcctactac atttggtgcc | 300 |
| ggtacaaaac tggagcttaa acgc | 324 |

<210> SEQ ID NO 6
<211> LENGTH: 987
<212> TYPE: DNA
<213> ORGANISM: Artificial Sequence
<220> FEATURE:
<223> OTHER INFORMATION: Synthetic Sequence

<400> SEQUENCE: 6

| agcaccaagg gcccatcggt cttccccctg gcaccctcct ccaagagcac ctctgggggc | 60 |
| acagcggccc tgggctgcct ggtcaaggac tacttccccg aaccggtgac ggtgtcgtgg | 120 |
| aactcaggcg ccctgaccag cggcgtgcac accttcccgg ctgtcctaca gtcctcagga | 180 |
| ctctactccc tcagcagcgt ggtgaccgtg ccctccagca gcttgggcac ccagacctac | 240 |
| atctgcaacg tgaatcacaa gcccagcaac accaaggtgg acaagaaagt tgagcccaaa | 300 |
| tcttgtgaca aaactcacac atgcccaccg tgcccagcac ctgaactcct ggggggaccg | 360 |
| tcagtcttcc tcttcccccc aaaacccaag gacaccctca tgatctcccg gacccctgag | 420 |
| gtcacatgcg tggtggtgga cgtgagccac gaagaccctg aggtcaagtt caactggtac | 480 |
| gtggacggcg tggaggtgca taatgccaag acaaagccgc gggaggagca gtacaacagc | 540 |
| acgtaccgtg tggtcagcgt cctcaccgtc ctgcaccagg actggctgaa tggcaaggag | 600 |
| tacaagtgca aggtctccaa caaagccctc ccagccccca tcgagaaaac catctccaaa | 660 |
| gccaaagggc agccccgaga accacaggtg tacaccctgc ccccatcccg ggaggagatg | 720 |
| accaagaacc aggtcagcct gacctgcctg gtcaaaggct tctatcccag cgacatcgcc | 780 |
| gtggagtggg agagcaatgg gcagccggag aacaactaca agaccacgcc tcccgtgctg | 840 |
| gactccgacg gctccttctt cctctacagc aagctcaccg tggacaagag caggtggcag | 900 |
| caggggaacg tcttctcatg ctccgtgatg catgaggctc tgcacaacca ctacacgcag | 960 |

```
aagagcctct ccctgtctcc gggtaaa                                       987
```

<210> SEQ ID NO 7
<211> LENGTH: 321
<212> TYPE: DNA
<213> ORGANISM: Artificial Sequence
<220> FEATURE:
<223> OTHER INFORMATION: Synthetic Sequence
<400> SEQUENCE: 7

```
ggtcagccca aggctgcccc ctcggtcact ctgttcccgc cctcctctga ggagcttcaa    60
gccaacaagg ccacactggt gtgtctcata agtgacttct acccgggagc cgtgacagtg   120
gcctggaagg cagatagcag ccccgtcaag gcgggagtgg agaccaccac accctccaaa   180
caaagcaaca caagtacgc ggccagcagc tatctgagcc tgacgcctga gcagtggaag    240
tcccacagaa gctacagctg ccaggtcacg catgaaggga gcaccgtgga aagacagtg    300
gccctacag aatgttcata g                                              321
```

<210> SEQ ID NO 8
<211> LENGTH: 589
<212> TYPE: DNA
<213> ORGANISM: Artificial Sequence
<220> FEATURE:
<223> OTHER INFORMATION: Synthetic Sequence
<400> SEQUENCE: 8

```
aatcaacctc tggattacaa aatttgtgaa agattgactg gtattcttaa ctatgttgct    60
ccttttacgc tatgtggata cgctgctta atgcctttgt atcatgctat tgcttcccgt    120
atggctttca ttttctcctc cttgtataaa tcctggttgc tgtctcttta tgaggagttg   180
tggcccgttg tcaggcaacg tggcgtggtg tgcactgtgt ttgctgacgc aaccccact    240
ggttggggca ttgccaccac ctgtcagctc ctttccggga cttttgcttt tcccctccct   300
attgccacgg cggaactcat cgccgcctgc cttgcccgct gctggacagg ggctcggctg   360
ttgggcactg acaattccgt ggtgttgtcg gggaaatcat cgtcctttcc ttggctgctc   420
gcctgtgttg ccacctggat tctgcgcggg acgtccttct gctacgtccc ttcggccctc   480
aatccagcgg accttccttc ccgcggcctg ctgccggctc tgcggcctct tccgcgtctt   540
cgccttcgcc ctcagacgag tcggatctcc ctttgggccg cctccccgc                589
```

<210> SEQ ID NO 9
<211> LENGTH: 8104
<212> TYPE: DNA
<213> ORGANISM: Artificial Sequence
<220> FEATURE:
<223> OTHER INFORMATION: Synthetic Sequence
<400> SEQUENCE: 9

```
ctgcgcgctc gctcgctcac tgaggccgcc cgggcaaagc ccgggcgtcg ggcgaccttt    60
ggtcgcccgg cctcagtgag cgagcgagcg cgcagagagg gagtggccaa ctccatcact   120
aggggttcct tgtagttaat gattaacccg ccatgctact tatctacgta gccatgctct   180
aggacattga ttattgacta gtggagttcc gcgttacata acttacggta aatggcccgc   240
ctggctgacc gcccaacgac ccccgcccat tgacgtcaat aatgacgtat gttcccatag   300
taacgccaat agggactttc cattgacgtc aatgggtgga gtatttacgg taaactgccc   360
acttggcagt acatcaagtg tatcatatgc caagtacgcc ccctattgac gtcaatgacg   420
```

-continued

```
gtaaatggcc cgcctggcat tatgcccagt acatgacctt atgggacttt cctacttggc    480
agtacatcta cgtattagtc atcgctatta ccatggtcga ggtgagcccc acgttctgct    540
tcactctccc catctccccc ccctccccac ccccaatttt gtatttattt attttttaat    600
tattttgtgc agcgatgggg gcggggggg ggggggcgc gcgccaggcg gggcggggcg     660
gggcgagggg cggggcgggg cgaggcggag aggtgcggcg gcagccaatc agagcggcgc    720
gctccgaaag tttccttta tggcgaggcg gcggcggcgg cggccctata aaaagcgaag    780
cgcgcggcgg gcgggagtcg ctgcgcgctg ccttcgcccc gtgccccgct ccgccgccgc    840
ctcgcgccgc ccgccccggc tctgactgac cgcgttacta aaacaggtaa gtccggcctc    900
cgcgccgggt tttggcgcct cccgcgggcg ccccccctcct cacggcgagc gctgccacgt    960
cagacgaagg gcgcagcgag cgtcctgatc cttcgcccg gacgctcagg acagcggccc    1020
gctgctcata agactcggcc ttagaacccc agtatcagca gaaggacatt ttaggacggg    1080
acttgggtga ctctagggca ctggttttct ttccagagag cggaacaggc gaggaaaagt    1140
agtcccttct cggcgattct gcggagggat ctccgtgggg cggtgaacgc cgatgatgcc    1200
tctactaacc atgttcatgt tttctttttt tttctacagg tcctgggtga cgaacagggt    1260
accgccacca tggcgacggg ttcaagaact tccctacttc ttgcatttgg cctgctttgt    1320
ttgccgtggt tacaggaggg ctcggcacag gtacaactga aacaaagcgg gcctgggctg    1380
gtccagccat cccaaagttt gtccataact tgcactgtta gtggttttag cttgaccaat    1440
tacggggtgc attgggtaag acagagtcct ggtaagggcc tcgaatggct gggcgtgata    1500
tggtcaggcg gcaatactga ctacaatact ccatttacca gcagattgtc catcaataaa    1560
gataattcta aaagccaggt attctttaag atgaactctc tgcagtccaa tgatactgca    1620
atttattact gtgcccgagc acttacctac tacgattacg agttcgcata ctggggccag    1680
ggtaccctcg tgaccgtatc tgcagcgagc accaagggcc catcggtctt ccccctggca    1740
ccctcctcca agagcacctc tggggcaca gcggccctgg gctgcctggt caaggactac    1800
ttccccgaac cggtgacggt gtcgtggaac tcaggcgccc tgaccagcgg cgtgcacacc    1860
ttcccggctg tcctacagtc ctcaggactc tactccctca gcagcgtggt gaccgtgccc    1920
tccagcagct tgggcaccca gacctacatc tgcaacgtga atcacaagcc cagcaacacc    1980
aaggtggaca gaaagttga gcccaaatct tgtgacaaaa ctcacacatg cccaccgtgc    2040
ccagcacctg aactcctggg gggaccgtca gtcttcctct tccccccaaa acccaaggac    2100
accctcatga tctcccggac ccctgaggtc acatgcgtgg tggtggacgt gagccacgaa    2160
gaccctgagg tcaagttcaa ctggtacgtg gacggcgtgg aggtgcataa tgccaagaca    2220
aagccgcggg aggagcagta caacagcacg taccgtgtgg tcagcgtcct caccgtcctg    2280
caccaggact ggctgaatgg caaggagtac aagtgcaagg tctccaacaa agccctccca    2340
gcccccatcg agaaaaccat ctccaaagcc aaagggcagc cccgagaacc acaggtgtac    2400
accctgcccc catcccggga ggagatgacc aagaaccagg tcagcctgac ctgcctggtc    2460
aaaggcttct atcccagcga catcgccgtg gagtgggaga gcaatgggca gccggagaac    2520
aactacaaga ccacgcctcc cgtgctggac tccgacggct ccttcttcct ctacagcaag    2580
ctcaccgtgg acaagagcag gtggcagcag gggaacgtct tctcatgctc cgtgatgcat    2640
gaggctctgc acaaccacta cacgcagaag agcctctccc tgtctccggg taaacgaaaa    2700
agaagatcag gttcgggtgc gccagtaaag cagacattaa actttgattt gctgaaactt    2760
gcaggtgatg tagagtcaaa tccaggtcca atggcaacag ggagccgaac ctctctgctc    2820
```

```
cttgctttcg ggctcctttg cctaccgtgg ctccaagagg gctcggcaga tatccttctg   2880
actcaatccc ctgtgattct gtcagtgtca ccaggggaaa gggtcagttt ttcatgtcgc   2940
gcatctcaaa gcattggcac taacatccac tggtaccaac aacgcacaaa cggaagtccc   3000
cgcttgctca tcaagtatgc aagcgaatca atcagcggga tcccttccag gttcagtggt   3060
agtgggagtg gtacagattt cactctctca attaacagcg tagagtccga ggacatcgcc   3120
gactattatt gccaacagaa caacaactgg cctactacat tggtgccgg tacaaaactg    3180 gagcttaaac gcggtcagcc caaggctgcc ccctcggtca ctctgttccc gccctcctct   3240
gaggagcttc aagccaacaa ggccacactg gtgtgtctca taagtgactt ctacccggga   3300
gccgtgacag tggcctggaa ggcagatagc agcccgtca aggcgggagt ggagaccacc    3360
acaccctcca acaaagcaa caacaagtac gcggccagca gctatctgag cctgacgcct    3420
gagcagtgga agtcccacag aagctacagc tgccaggtca cgcatgaagg gagcaccgtg   3480
gagaagacag tggcccctac agaatgttca tagtctagaa taatcaacct ctggattaca   3540
aaatttgtga agattgact ggtattctta actatgttgc tccttttacg ctatgtggat     3600
acgctgcttt aatgcctttg tatcatgcta ttgcttcccg tatggctttc attttctcct   3660
ccttgtataa atcctggttg ctgtctcttt atgaggagtt gtggcccgtt gtcaggcaac   3720
gtggcgtggt gtgcactgtg tttgctgacg caacccccac tggttgggc attgccacca    3780 cctgtcagct cctttccggg actttcgctt tccccctccc tattgccacg cggaactca    3840 tcgccgcctg ccttgcccgc tgctggacag gggctcggct gttgggcact gacaattccg   3900
tggtgttgtc ggggaaatca tcgtcctttc cttggctgct cgcctgtgtt gccacctgga   3960
ttctgcgcgg gacgtccttc tgctacgtcc cttcggccct caatccagcg gaccttcctt   4020
cccgcggcct gctgccggct ctgcggcctc ttccgcgtct tcgccttcgc cctcagacga   4080
gtcggatctc cctttgggcc gcctccccgc ctaagcttat cgataccgtc gagatctaac   4140
ttgtttattg cagcttataa tggttacaaa taaagcaata gcatcacaaa tttcacaaat   4200
aaagcatttt tttcactgca ttctagttgt ggtttgtcca aactcatcaa tgtatcttat   4260
catgtctgga tctcgacctc gactagagca tggctacgta dataagtagc atggcgggtt   4320
aatcattaac tacaaggaac ccctagtgat ggagttggcc actccctctc tgcgcgctcg   4380
ctcgctcact gaggccgggc gaccaaaggt cgcccgacgc ccgggctttg cccgggcggc   4440
ctcagtgagc gagcgagcgc gccagctggc gtaatagcga agaggcccgc accgatcgcc   4500
cttcccaaca gttgcgcagc ctgaatggcg aatggaattc cagacgattg agcgtcaaaa   4560
tgtaggtatt tccatgagcg ttttttcctgt tgcaatggct ggcggtaata ttgttctgga   4620
tattaccagc aaggccgata gtttgagttc ttctactcag gcaagtgatg ttattactaa   4680
tcaaagaagt attgcgacaa cggttaattt gcgtgatgga cagactcttt tactcggtgg   4740
cctcactgat tataaaaaca cttctcagga ttctggcgta ccgttcctgt ctaaaatccc   4800
tttaatcggc ctcctgttta gctcccgctc tgattctaac gaggaaagca cgttatacgt   4860
gctcgtcaaa gcaaccatag tacgcgccct gtagcggcgc attaagcgcg gcgggtgtgg   4920
tggttacgcg cagcgtgacc gctacacttg ccagcgccct agcgcccgct cctttcgctt   4980
tcttcccttc ctttctcgcc acgttcgccg gctttccccg tcaagctcta aatcggggc    5040 tccctttagg gttccgattt agtgctttac ggcacctcga ccccaaaaaa cttgattagg   5100
gtgatggttc acgtagtggg ccatcgccct gatagacggt ttttcgccct ttgacgttgg   5160
```

```
agtccacgtt ctttaatagt ggactcttgt tccaaactgg aacaacactc aaccctatct   5220
cggtctattc ttttgattta aagggatttt tgccgatttc ggcctattgg ttaaaaaatg   5280
agctgattta acaaaaattt aacgcgaatt ttaacaaaat attaacgttt acaatttaaa   5340
tatttgctta tacaatcttc ctgttttttgg ggcttttctg attatcaacc ggggtacata   5400
tgattgacat gctagtttta cgattaccgt tcatcgattc tcttgtttgc tccagactct   5460
caggcaatga cctgatagcc tttgtagaga cctctcaaaa atagctaccc tctccggcat   5520
gaatttatca gctagaacgg ttgaatatca tattgatggt gatttgactg tctccggcct   5580
ttctcacccg tttgaatctt tacctacaca ttactcaggc attgcattta aaatatatga   5640
gggttctaaa aattttttatc cttgcgttga ataaaggct tctcccgcaa aagtattaca   5700
gggtcataat gttttttggta caaccgattt agctttatgc tctgaggctt tattgcttaa   5760
ttttgctaat tctttgcctt gcctgtatga tttattggat gttggaattc ctgatgcggt   5820
attttctcct tacgcatctg tgcggtattt cacaccgcat atggtgcact ctcagtacaa   5880
tctgctctga tgccgcatag ttaagccagc cccgacaccc gccaacaccc gctgacgcgc   5940
cctgacgggc ttgtctgctc ccggcatccg cttacagaca agctgtgacc gtctccggga   6000
gctgcatgtg tcagaggttt tcaccgtcat caccgaaacg cgcgagacga aagggcctcg   6060
tgatacgcct atttttatag gttaatgtca tgataataat ggtttcttag acgtcaggtg   6120
gcacttttcg gggaaatgtg cgcggaaccc ctatttgttt attttcctaa atacattcaa   6180
atatgtatcc gctcatgaga caataaccct gataaatgct tcaataatat tgaaaaagga   6240
agagtatgag tattcaacat ttccgtgtcg cccttattcc cttttttgcg cattttgcc   6300
ttcctgtttt tgctcaccca gaaacgctgg tgaaagtaaa agatgctgaa gatcagttgg   6360
gtgcacgagt gggttacatc gaactggatc tcaacagcgg taagatcctt gagagttttc   6420
gccccgaaga acgttttcca atgatgagca cttttaaagt tctgctatgt ggcgcggtat   6480
tatcccgtat tgacgccggg caagagcaac tcggtcgccg catacactat tctcagaatg   6540
acttggttga gtactcacca gtcacagaaa agcatcttac ggatggcatg acagtaagag   6600
aattatgcag tgctgccata accatgagtg ataacactgc ggccaactta cttctgacaa   6660
cgatcggagg accgaaggag ctaaccgctt ttttgcacaa catgggggat catgtaactc   6720
gccttgatcg ttgggaaccg gagctgaatg aagccatacc aaacgacgag cgtgacacca   6780
cgatgcctgt agcaatggca acaacgttgc gcaaactatt aactggcgaa ctacttactc   6840
tagcttcccg gcaacaatta atagactgga tggaggcgga taaagttgca ggaccacttc   6900
tgcgctcggc ccttccggct ggctggttta ttgctgataa atctggagcc ggtgagcgtg   6960
ggtctcgcgg tatcattgca gcactggggc cagatggtaa gccctcccgt atcgtagtta   7020
tctacacgac ggggagtcag gcaactatgg atgaacgaaa tagacagatc gctgagatag   7080
gtgcctcact gattaagcat tggtaactgt cagaccaagt ttactcatat atactttaga   7140
ttgatttaaa acttcatttt taatttaaaa ggatctaggt gaagatcctt tttgataatc   7200
tcatgaccaa aatcccttaa cgtgagtttt cgttccactg agcgtcagac cccgtagaaa   7260
agatcaaagg atcttcttga gatccttttt tctgcgcgt aatctgctgc ttgcaaacaa   7320
aaaaaccacc gctaccagcg gtggtttgtt tgccggatca agagctacca actctttttc   7380
cgaaggtaac tggcttcagc agagcgcaga taccaaatac tgtccttcta gtgtagccgt   7440
agttaggcca ccacttcaag aactctgtag caccgcctac atacctcgct ctgctaatcc   7500
tgttaccagt ggctgctgcc agtggcgata agtcgtgtct taccgggttg gactcaagac   7560
```

```
gatagttacc ggataaggcg cagcggtcgg gctgaacggg gggttcgtgc acacagccca    7620
gcttggagcg aacgacctac accgaactga gatacctaca gcgtgagcta tgagaaagcg    7680
ccacgcttcc cgaagggaga aaggcggaca ggtatccggt aagcggcagg gtcggaacag    7740
gagagcgcac gagggagctt ccaggggaa acgcctggta tctttatagt cctgtcgggt     7800
ttcgccacct ctgacttgag cgtcgatttt tgtgatgctc gtcagggggg cggagcctat    7860
ggaaaaacgc cagcaacgcg gccttttac ggttcctggc cttttgctgg ccttttgctc     7920
acatgttctt tcctgcgtta tcccctgatt ctgtggataa ccgtattacc gcctttgagt    7980
gagctgatac cgctcgccgc agccgaacga ccgagcgcag cgagtcagtg agcgaggaag    8040
cggaagagcg cccaatacgc aaaccgcctc tccccgcgcg ttggccgatt cattaatgca    8100
gcag                                                                 8104
```

COMPOSITIONS AND METHOD OF MAKING A COMPLEX ABLE TO INCREASE PRODUCTION OF A CETUXIMAB-LIKE PROTEIN (CLP) IN A TARGET CELL

SEQUENCE LISTING

This application contains a sequence listing electronically submitted via efs web to the United States Patent and Trademark Office as an ascii text file entitled "A8145603US_st25.txt" created on May 4, 2021 and having a size of 16.9 KB. The information contained in the sequence listing is incorporated by reference herein.

TECHNICAL FIELD

The present disclosure generally relates to compositions and methods for regulating tumor cell growth. In particular, the present disclosure relates to compositions and methods for regulating endogenous production of an inhibitor of growth factors that facilitate cancer cell DNA synthesis and cancer cell growth.

BACKGROUND

Epidermal Growth Factor Receptor (EGFR) is a cell surface receptor that spans the cell membrane with an extracellular ligand-binding domain and an intracellular signaling domain. Upon a binding event with a ligand, such as epidermal growth factor and transforming growth factor alpha, EGFR transitions to an active state. In the active state, the EGFR may undergo a dimerization event, which then activates the intracellular signaling domain. In particular, the activated intracellular signaling domain activates a protein-tyrosine kinase enzyme, which activates one or more intracellular cell signaling pathways to ultimately activate synthesis of deoxyribonucleic acid (DNA) synthesis and, in particular, genes associated with cell growth and proliferation.

It is known that dysregulation of EGFR, such as through mutant EGFR phenotypes or otherwise, can result in overstimulation, also referred to as amplification and upregulation, and this overstimulation has been causally linked to various cancers. In effect, the EGFR signaling pathway results in excessive DNA synthesis in tumor cells and, therefore, growth and proliferation of the tumor cells.

In efforts to treat such dysregulated-EGFR related cancers, a number of monoclonal antibody (mAB) protein therapies have been developed. In general, the mAB protein therapies can bind to the extracellular ligand-binding domain inhibit EGFR and that prevents a binding event with any stimulatory ligand, ultimately inhibiting the intracellular signaling and DNA synthesis activation.

Currently, mAB protein therapies require that a patient attend a clinic or hospital setting for intravenous administration. This intravenous administration can be costly, disruptive to the patient's life and potentially expose the patient to a greater risk of acquiring a healthcare-acquired nosocomial infection.

SUMMARY

Some embodiments of the present disclosure relate to compositions and methods that cause a subject to produce a monoclonal antibody (mAB) protein that can act as a targeted therapy for cancer. In some embodiments of the present disclosure, the mAB binds to and inhibits Epidermanl Growth Factor Receptor (EGFR) by binding to the extracellular ligand-binding domain of EGFR. This mAB binding blocks the EGFR's ability to bind other stimulatory ligands and it may reduce excessive deoxyribonucleic acid (DNA) synthesis in tumor cells and, therefore, growth and proliferation of the tumor cells. Some embodiments of the present disclosure relate to compositions and methods that cause a subject to produce a mAB that is substantially similar, or similar or the same as Cetuximab, referred to herein as a Cetuximab-like protein (CLP). In some embodiments of the present disclosure, the subject's production of the CLP is endogenous. The CLP may be bioavailable and functionally equivalent to an exogenously administered Cetuximab.

In some embodiments of the present disclosure, the compositions described herein comprise a vector of plasmid DNA that includes an insert sequence of nucleic acids. The insert sequence encodes for the production of the CLP and the insert sequence may also include a backbone sequence of nucleic acids that facilitates introduction of the insert sequence into one or more of a subject's cells. Within the subject's cells, the insert sequence is expressed and/or replicated. Expression of the insert sequence by one or more cells of the subject results in an increased production of the CLP by the subject. In some embodiments of the present disclosure, the methods that upregulate the production of CLP and to methods of manufacturing and administering the compositions that result in a subject's increased production of CLP.

Some embodiments of the present disclosure relate to compositions and methods that can be used as a therapy or a treatment for a subject that has a condition associated with increased growth and/or proliferation of tumor cells. The embodiments of the present disclosure may result in a subject who receives such therapy or treatment to increase production of the CLP. The CLP may interfere with the biological activity of EGFR. Some embodiments of the present disclosure relate to a recombinant virus vector (RVV) that forms part of such therapy or treatment. The RVV comprises a nucleotide sequence encoding production of the CLP so that a recipient of the RVV may then produce the CLP from their own cells.

Some embodiments of the present disclosure relate to a composition that comprises a nucleotide sequence according to the present disclosure (SEQ ID No. 9) of which at least a portion can be expressed in a target cell.

Some embodiments of the present disclosure relate to an insert for use with an RVV, wherein the insert has a nucleotide sequence has one or more of SEQ ID No. 1, SEQ ID No. 2, SEQ ID No. 3, SEQ ID No. 4, SEQ ID No. 5. SEQ ID No. 6, SEQ ID No. 7, or SEQ ID No. 8.

Some embodiments of the present disclosure relate to the insert with one or more of SEQ ID No. 1, SEQ ID No. 2, SEQ ID No. 3, SEQ ID No. 4, SEQ ID No. 5, SEQ ID No. 6. SEQ ID No. 7, or SEQ ID No. 8 for use with an RVV.

Some embodiments of the present disclosure relate to a method of making an agent/target cell complex, the method comprising a step of administering a therapeutically effective amount of the agent to a subject, wherein the agent/target cell complex increases the subject's production of the CLP.

Some embodiments of the present disclosure relate to a pharmaceutical agent that comprises an agent, a pharmaceutically acceptable carrier and/or an excipient. Administering the pharmaceutical agent to a subject may increase the subject's production of the CLP.

Some embodiments of the present disclosure relate to a method of treating a condition. The method comprises a step of administering to a subject a therapeutically effective amount of an agent that upregulates the subject's production of the CLP and the CLP may ameliorate the condition. In some embodiments of the present disclosure, the condition is cancer.

Some embodiments of the present disclosure relate to a use of an agent for treating a condition, wherein the agent upregulates the subject's production of the CLP and the CLP may ameliorate the condition. In some embodiments of the present disclosure, the condition is cancer.

Embodiments of the present disclosure relate to at least one approach for inducing endogenous production of the CLP. A first approach utilizes one or more gene vectors containing nucleotide sequences for increasing the endogenous production of the CLP. The one or more vectors can be administered to a subject to increase the subject's production of the CLP.

In some embodiments of the present disclosure, following administration of the agent the CLP may be produced within the subject's cells as a precursor CLP protein that can be subjected to one or more post-translational modification processes, which results in subject cells that are producing the precursor CLP protein to produce a final CLP product that is bioavailable and functional. In some embodiments of the present disclosure, the CLP product may be capable of participating in a binding event with a specific family of receptor proteins, such as EGFR. Without being bound by any particular theory, when such a binding event occurs, the CLP product can act to prevent further ligands from binding to and/or activating EGFR.

BRIEF DESCRIPTION OF THE DRAWINGS

These and other features of the present disclosure will become more apparent in the following detailed description in which reference is made to the appended drawings.

FIG. 1 is a scatter plot that shows Human IgG expression, indicative of CLP expression, up to 28 days following administration of a vector, according to embodiments of the present disclosure, in mice.

DETAILED DESCRIPTION

Unless defined otherwise, all technical and scientific terms used herein have the meanings that would be commonly understood by one of skill in the art in the context of the present description. Although any methods and materials similar or equivalent to those described herein can also be used in the practice or testing of the present disclosure, the preferred methods and materials are now described. All publications mentioned herein are incorporated herein by reference to disclose and describe the methods and/or materials in connection with which the publications are cited.

As used herein, the singular forms "a", "an", and "the" include plural references unless the context clearly dictates otherwise. For example, reference to "an agent" includes one or more agents and reference to "a subject" or "the subject" includes one or more subjects.

As used herein, the terms "about" or "approximately" refer to within about 25%, preferably within about 20%, preferably within about 15%, preferably within about 10%, preferably within about 5% of a given value or range. It is understood that such a variation is always included in any given value provided herein, whether or not it is specifically referred to.

As used herein, the term "activity" is used interchangeably with the term "functionality" and both terms refer to the physiologic action of biomolecule.

As used herein, the term "agent" refers to a substance that, when administered to a subject, causes one or more chemical reactions and/or one or more physical reactions and/or or one or more physiological reactions and/or one or more immunological reactions in the subject. In some embodiments of the present disclosure, the agent is a plasmid vector, such as a recombinant virus vector (RVV) as described herein.

As used herein, the term "ameliorate" refers to improve and/or to make better and/or to make more satisfactory.

As used herein, the term "biomolecule" refers to a carbohydrate, a protein, an amino acid sequence, a nucleic acid, a lipid, a primary metabolite, a secondary metabolite or another metabolite that is found within a subject. A biomolecule may be endogenous or exogenous to a subject.

As used herein, the term "cell" refers to a single cell as well as a plurality of cells or a population of the same cell type or different cell types. Administering an agent to a cell includes in vivo, in vitro and ex vivo administrations and/or combinations thereof.

As used herein, the term "complex" refers to an association, either direct or indirect, between one or more particles of an agent and one or more target cells. In some embodiments, reference to a complex includes uptake of one or more particles of the agent by the target cell. In other embodiments, reference to a complex may include uptake and expression by the target cell of one or more nucleotide sequences carried by the particles of the agent. This association results in a change in the metabolism of the target cell. As used herein, the phrase "change in metabolism" refers to an increase or a decrease in the one or more target cells' production of deoxyribonucleic acid (DNA), ribonucleic acid (RNA), one or more proteins, and/or any post-translational modifications of one or more proteins.

As used herein, the terms "dysregulation" and "dysregulated" refer to situations or conditions wherein homeostatic control systems have been disturbed and/or compromised so that one or more metabolic, physiologic and/or biochemical systems within a subject operate partially or entirely without said homeostatic control systems.

As used herein, the term "effector molecule" refers to a molecule within a subject that can directly or indirectly regulate the metabolic activity of a target cell by increasing or decreasing the production of DNA, RNA and/or amino-acid sequences and/or by increasing or decreasing any post-translational modifications of one or more proteins.

As used herein, the term "endogenous" refers to the production and/or modification of a molecule that originates within a cell of a subject.

As used herein, the term "excipient" refers to any substance, not itself an agent, which may be used as a component within a pharmaceutical composition or a medicament for administration of a therapeutically effective amount of the agent to a subject. Additionally, or alternatively, an excipient may, either alone or in combination with further chemical components, improve the handling and/or storage properties and/or permit or facilitate formation of a dose unit of the agent. Excipients include, but are not limited to, one or more of: a binder, a disintegrant, a diluent, a buffer, a taste enhancer, a solvent, a thickening agent, a gelling agent, a penetration enhancer, a solubilizing agent, a wetting agent, an antioxidant, a preservative, a surface active agent, a lubricant, an emollient, a substance that is added to mask or counteract a disagreeable odor, fragrance or taste, a substance added to improve appearance or texture of the composition and/or a substance that is used to form the pharmaceutical compositions or medicaments. Any such excipients can be used in any dosage forms according to the present disclosure. The foregoing classes of excipients are not meant to be exhaustive but are provided merely to be illustrative of what a person of skill in the art would know and would also recognize that additional types and combinations of excipients may be used to achieve delivery of a therapeutically effective amount of the agent to a subject through one or more routes of administration.

As used herein, the term "exogenous" refers to a molecule that is within a subject but that did not originate within the subject.

As used herein, the terms "inhibit", "inhibiting", and "inhibition" refer to a decrease in activity, response, or other biological parameter of a biologic process, disease, disorder or symptom thereof. This can include but is not limited to the complete ablation of the activity, response, condition, or disease. This may also include, for example, a 10% reduction in the activity, response, condition, or disease as compared to the native or control level. Thus, the reduction can be a 10%, 20%, 30%, 40%, 50%, 60%, 70%, 80%, 900%, 100%, or any amount of reduction in between the specifically recited percentages, as compared to native or control levels.

As used herein, the term "medicament" refers to a medicine and/or pharmaceutical composition that comprises the agent and that can promote recovery from a disease, disorder or symptom thereof and/or that can prevent a disease, disorder or symptom thereof and/or that can inhibit the progression of a disease, disorder, or symptom thereof.

As used herein, the term "patient" refers to a subject that is afflicted with a disease or disorder. The term "patient" includes human and veterinary subjects.

As used herein, the term "pharmaceutical composition" means any composition comprising, but not necessarily limited to, an agent to be administered a subject in need of therapy or treatment of a disease, disorder or symptom thereof. Pharmaceutical compositions may include additives such as pharmaceutically acceptable carriers, pharmaceutically accepted salts, excipients and the like. Pharmaceutical compositions may also additionally include one or more further active ingredients such as antimicrobial agents, anti-inflammatory agents, anaesthetics, analgesics, and the like.

As used herein, the term "pharmaceutically acceptable carrier" refers to an essentially chemically inert and non-toxic component within a pharmaceutical composition or medicament that does not inhibit the effectiveness and/or safety of the agent. Some examples of pharmaceutically acceptable carriers and their formulations are described in Remington (1995, The Science and Practice of Pharmacy (19th ed.) ed. A. R. Gennaro, Mack Publishing Company, Easton, Pa.), the disclosure of which is incorporated herein by reference. Typically, an appropriate amount of a pharmaceutically acceptable carrier is used in the formulation to render said formulation isotonic. Examples of suitable pharmaceutically acceptable carriers include, but are not limited to: saline solutions, glycerol solutions, ethanol, N-(1(2, 3-dioleyloxy)propyl)-N,N,N-trimethylammonium chloride (DOTMA), dioleolphosphotidylethanolamine (DOPE), and liposomes. Such pharmaceutical compositions contain a therapeutically effective amount of the agent, together with a suitable amount of one or more pharmaceutically acceptable carriers and/or excipients so as to provide a form suitable for proper administration to the subject. The formulation should suit the route of administration. For example, oral administration may require enteric coatings to protect the agent from degrading within portions of the subject's gastrointestinal tract. In another example, injectable routes of administration may be administered in a liposomal formulation to facilitate transport throughout a subject's vascular system and to facilitate delivery across cell membranes of targeted intracellular sites.

As used herein, the phrases "prevention of" and "preventing" refer to avoiding the onset or progression of a disease, disorder, or a symptom thereof.

As used herein, the terms "production", "producing" and "produce" refer to the synthesis and/or replication of DNA, the transcription of one or more sequences of RNA, the translation of one or more amino acid sequences, the post-translational modifications of an amino-acid sequence, and/or the production of one or more regulatory molecules that can influence the production and/or functionality of an effector molecule or an effector cell. For clarity, "production" is also be used herein to refer to the functionality of a regulatory molecule, unless the context reasonably indicates otherwise.

As used herein, the terms "promote", "promotion" and "promoting" refer to an increase in an activity, response, condition, disease process, or other biological parameter. This can include, but is not limited to, the initiation of the activity, response, condition, or disease process. This may also include, for example, a 10% increase in the activity, response, condition, or disease as compared to the native or control level. Thus, the increase in an activity, response, condition, disease, or other biological parameter can be 10%, 20%, 30%, 40%, 50%, 60%, 70%, 80%, 90%, 100%, or more, including any amount of increase in between the specifically recited percentages, as compared to native or control levels.

As used herein, the term "prophylactic administration" refers to the administration of any composition to a subject, in the absence of any symptom or indication of a disease or disorder, to prevent the occurrence and/or progression of the disease or disorder within the subject.

As used herein, the terms "signal molecule", "signalling molecule" and "regulatory molecule" can be used interchangeably and refer to a molecule that can directly or indirectly affect the production and/or functionality of an effector molecule or effector cell. Signal molecules can be enzymes or other types of biomolecules that can act as a direct ligand on a target cell or they may influence the levels or functionality of a downstream ligand or a receptor for a ligand.

As used herein, the term "subject" refers to any therapeutic target that receives the agent. The subject can be a vertebrate, for example, a mammal including a human. The term "subject" does not denote a particular age or sex. The term "subject" also refers to one or more cells of an organism, an in vitro culture of one or more tissue types, an in vitro culture of one or more cell types, ex % vivo preparations, and for a sample of biological materials such as tissue and/or biological fluids.

As used herein, the term "target cell" refers to one or more cells and/or cell types that are deleteriously affected, either directly or indirectly, by a dysregulated immune system and/or a disease process. The term "target cell" also refers to cells that are not deleteriously affected but that are cells in which it is desired that the agent interacts.

As used herein, the term "therapeutically effective amount" refers to the amount of the agent used that is of sufficient quantity to ameliorate, treat and/or inhibit one or more of a disease, disorder or a symptom thereof. The "therapeutically effective amount" will vary depending on the agent used, the route of administration of the agent and the severity of the disease, disorder or symptom thereof. The subject's age, weight and genetic make-up may also influence the amount of the agent that will be a therapeutically effective amount.

As used herein, the terms "treat". "treatment" and "treating" refer to obtaining a desired pharmacologic and/or physiologic effect. The effect may be prophylactic in terms of completely or partially preventing an occurrence of a disease, disorder or symptom thereof and/or the effect may be therapeutic in providing a partial or complete amelioration or inhibition of a disease, disorder, or symptom thereof. Additionally, the term "treatment" refers to any treatment of a disease, disorder, or symptom thereof in a subject and includes: (a) preventing the disease from occurring in a subject which may be predisposed to the disease but has not yet been diagnosed as having it; (b) inhibiting the disease, i.e., arresting its development; and, (c) ameliorating the disease.

As used herein, the terms "unit dosage form" and "unit dose" refer to a physically discrete unit that is suitable as a unitary dose for patients. Each unit contains a predetermined quantity of the agent and optionally, one or more suitable pharmaceutically acceptable carriers, one or more excipients, one or more additional active ingredients, or combinations thereof. The amount of agent within each unit is a therapeutically effective amount.

In embodiments of the present disclosure, the pharmaceutical compositions disclosed herein comprise an agent as described above in a total amount by weight of the composition of about 0.1% to about 95%. For example, the amount of the agent by weight of the pharmaceutical composition may be about 0.1%, about 0.2%, about 0.3%, about 0.4%, about 0.5%, about 0.6%, about 0.7%, about 0.8%, about 0.9%, about 1%, about 1.1%, about 1.2%, about 1.3%, about 1.4%, about 1.5%, about 1.6%, about 1.7%, about 1.8%, about 1.9%, about 2%, about 2.1%, about 2.2%, about 2.3%, about 2.4%, about 2.5%, about 2.6%, about 2.7%, about 2.8%, about 2.9%, about 3%, about 3.1%, about 3.2%, about 3.3%, about 3.4%, about 3.5%, about 3.6%, about 3.7%, about 3.8%, about 3.9%, about 4%, about 4.1%, about 4.2%, about 4.3%, about 4.4%, about 4.5%, about 4.6%, about 4.7%, about 4.8%, about 4.9%, about 5%, about 5.1%, about 5.2%, about 5.3%, about 5.4%, about 5.5%, about 5.6%, about 5.7%, about 5.8%, about 5.9%, about 6%, about 6.1%, about 6.2%, about 6.3%, about 6.4%, about 6.5%, about 6.6%, about 6.7%, about 6.8%, about 6.9%, about 7%, about 7.1%, about 7.2%, about 7.3%, about 7.4%, about 7.5%, about 7.6%, about 7.7%, about 7.8%, about 7.9%, about 8%, about 8.1%, about 8.2%, about 8.3%, about 8.4%, about 8.5%, about 8.6%, about 8.7%, about 8.8%, about 8.9%, about 9%, about 9.1%, about 9.2%, about 9.3%, about 9.4%, about 9.5%, about 9.6%, about 9.7%, about 9.8%, about 9.9%, about 10%, about 11%, about 12%, about 13%, about 14%, about 15%, about 16%, about 17%, about 18%, about 19%, about 20%, about 25%, about 30%, about 35%, about 40%, about 45%, about 50%, about 55%, about 60%, about 65%, about 70%, about 75%, about 80%, about 85%, about 90% or about 95%.

Where a range of values is provided herein, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges, and are also, encompassed within the disclosure, subject to any specifically excluded limit in the stated range. Where the stated range includes one or both of the limits, ranges excluding either or both of those included limits are also included in the disclosure.

In some embodiments of the present disclosure, an agent is a plasmid vector for introducing into a target cell for reproduction or transcription of an insert that comprises one or more nucleotide sequences that are carried within the plasmid vector. In some embodiments of the present disclosure, the plasmid vector is a viral vector. In some embodiments of the present disclosure, the vector is an adeno-associated virus vector.

As used herein, the term "nucleotide sequence" is intended to also include a human codon optimized variant.

In some embodiments of the present disclosure, the insert comprises one or more nucleotide sequences that encode for production of a protein. The protein is substantially similar, or substantially the same, as a translational product of a gene whose expression results in increased production of a Cetuximab-like protein (CLP) that can reduce or inhibit EGER-mediated dysregulation of DNA synthesis of genes that relate to cell growth and proliferation in tumor cells. In some embodiments of the present disclosure, the CLP may be susceptible to one or more post-translational modification processes to create a CLP product that can bind with and inhibit EGFR. For clarity, references to CLP herein include references to the CLP product.

In some embodiments of the present disclosure, the CLP is substantially similar, or substantially the same, biofunctionality and bioavailability as Cetuximab that a subject could receive from an exogenous source.

The present disclosure relates to one or more agents, therapies, treatments, and methods of use of the agents and/or therapies and/or treatments for initiating or upregulating production of the CLP. Some embodiments of the present disclosure relate to methods for making a complex between at least one particle of an agent and at least one target cell of a subject for initiating or increasing production of the CLP within the subject. Therefore, the administration of the one or more vectors may increase the production of the precursor protein within one or more of a subject's cells. As such, the embodiments of the present disclosure can be used as a therapy or a treatment for a subject that has a condition whereby tumor cells have increased EGFR-mediated growth and proliferation.

In some embodiments of the present disclosure, the agent can be administered to the subject by an intravenous route, an intramuscular route, an intraperitoneal route, an intrathecal route, an intravesical route, a topical route, an intranasal route, a transmucosal route, a pulmonary route, and combinations thereof.

In some embodiments of the present disclosure, the agent can be administered to the subject by pipetting a dose of the agent into an in vitro cell culture, perfusing or immersing an ex vivo cell or tissue preparation with a solution that comprises the agent, mixing a biological fluid sample with a solution or substrate that comprises the agent, or combinations thereof.

Some embodiments of the present disclosure relate to an agent that can be administered to a subject with a condition that could benefit from an endogenous source of CLP. When a therapeutically effective amount of the agent is administered to the subject, one or more of the subject's cell may increase the translational production of the CLP.

In some embodiments of the present disclosure, the agent is a vector used for gene therapy. The gene therapy is useful for increasing the subject's endogenous production of the CLP. For example, the vector can contain one or more nucleotide sequences that that cause increased production of the CLP in the subject's cells where the vector is expressed.

In some embodiments of the present disclosure, the vector used for gene therapy is a virus that can be enveloped or not, replication effective or not, or combinations thereof. In some embodiments of the present disclosure, the vector is a virus that is not enveloped and not replication effective. In some embodiments of the present disclosure, the vector is a virus of the Paroviridae family. In some embodiments of the present disclosure, the vector is a virus of the genus Dependoparvaovirus, in some embodiments of the present disclosure, the vector is an adeno-associated virus (AAV). In some embodiments of the present disclosure, the vector is a recombinant AAV.

The embodiments of the present disclosure also relate to administering a therapeutically effective amount of the agent. In some embodiments of the present disclosure, the therapeutically effective amount of the agent that is administered to a patient is between about 10 and about $1 \times 10^{16}$, $TCID_{50}$/kg (50% tissue culture infective dose per kilogram of the patient's body weight). In some embodiments of the present disclosure, the therapeutically effective amount of the agent that is administered to the patient is about $1 \times 10^{13}$ $TCID_{50}$/kg. In some embodiments of the present disclosure, the therapeutically effective amount of the agent that is administered to a patient is measured in TPC/kg (total particle count of the agent per kilogram of the patient's body weight). In some embodiments the therapeutically effective amount of the agent is between about 10 and about $1 \times 10^{16}$ TCP/kg.

Some embodiments of the present disclosure relate to a method for making a complex within a subject. The method comprises a step of administering a therapeutically effective amount of the agent to the subject. The complex comprises at least one particle of the agent and one or more target cells. When the complex is formed, it affects a change in the metabolism of the one or more target cells, which results in the target cells starting and/or upregulating the production of the CLP. Examples of a target cell include but are not limited to: an innate immune cell, an acquired immune cell, an adrenal gland cell; a bile duct cell; a chondrocyte; a cochlear cell; a corneal cell; an endocardium cell; an endometrial cell; an endothelial cell; an epithelial cell; a fibroblast; a hair follicle cell; a hepatocyte; a lymph node cell; a mucosal cell; a myocyte; a neuron; a glomeruli cell; an optic nerve cell; an osteoblast; an ovarian tissue cell; a pancreatic islet beta cell; a pericardium cell; a platelet; a red blood cell (RBC); a retinal cell; a scleral cell; a Schwann cell; a T cell; a testicular tissue cell; a thyroid gland cell; a uveal cell; a tumor cell, or combinations thereof.

Some embodiments of the present disclosure relate to a therapy, or method of treating a condition, that can be administered to a subject with the condition. The therapy comprises a step of administering to the subject a therapeutically effective amount of an agent that will upregulate the subject's production of the CLP. The increased production of the CLP may result in increased levels of functional and bioavailable CLP, which may reduce deleterious effects of the condition upon the subject. For example, the CLP may reduce the development of new blood vessels in high metabolic-rate cells, such as tumor cells.

Below are examples of nucleotide sequences of each may be present in the insert. As will be appreciated by those skilled in the art, minor modifications, substitutions or replacements of a select few nucleotides or amino acids in the sequences provided below will not substantially impact the physiologic or biologic effect of such modified sequences, as compared to the sequences provided herein below. Any such modified sequences are also contemplated by the present disclosure as are all human codon optimized variants.

Some embodiments of the present disclosure relate to the following nucleotide sequence SEQ ID No. 1 (an inverted terminal repeat):

```
ctgcgcgctc gctcgctcac tgaggccgcc cgggcaaagc ccgggcgtcg ggcgaccttt   60
ggtcgcccgg cctcagtgag cgagcgagcg cgcagagagg gagtggccaa ctccatcact  120
aggggttcct                                                          130
```

Some embodiments of the present disclosure relate to the following nucleotide sequence SEQ ID No. 2 (an inverted terminal repeat):

```
aggaacccct agtgatggag ttggccactc cctctctgcg cgctcgctcg ctcactgagg   60
ccgggcgacc aaaggtcgcc cgacgcccgg gctttgcccg ggcggcctca gtgagcgagc  120
gagcgcgc                                                           128
```

Some embodiments of the present disclosure relate to the following nucleotide sequence SEQ ID No. 3 (a CASI promoter):

```
ggagttccgc gttacataac ttacggtaaa tggcccgcct ggctgaccgc ccaacgaccc   60
ccgcccattg acgtcaataa tgacgtatgt tcccatagta acgccaatag ggactttcca  120
ttgacgtcaa tgggtggagt atttacggta aactgcccac ttggcagtac atcaagtgta  180
tcatatgcca agtacgcccc ctattgacgt caatgacggt aaatggcccg cctggcatta  240
```

-continued

```
tgcccagtac atgacctta t gggactttcc tacttggcag tacatctacg tattagtcat  300
cgctattacc atggtcgagg tgagccccac gttctgcttc actctcccca tctcccccc   360 ctccccaccc ccaattttgt atttatttat tttttaatta ttttgtgcag cgatgggggc  420
gggggggggg gggggcgcgc gccaggcggg gcggggcggg gcgaggggcg gggcggggcg  480
aggcggagag gtgcggcggc agccaatcag agcggcgcgc tccgaaagtt tccttttatg  540
gcgaggcggc ggcggcggcg gccctataaa aagcgaagcg cgcggcgggc gggagtcgct  600
gcgcgctgcc ttcgcccgt gccccgctcc gccgccgcct cgccgcgccc gccccggctc   660
tgactgaccg cgttactaaa acaggtaagt ccggcctccg cgccgggttt tggcgcctcc  720
cgcgggcgcc cccctcctca cggcgagcgc tgccacgtca gacgaagggc gcagcgagcg  780
tcctgatcct tccgcccgga cgctcaggac agcggcccgc tgctcataag actcggcctt  840
agaaccccag tatcagcaga aggacatttt aggacgggac ttgggtgact ctagggcact  900
ggttttcttt ccagagagcg aacaggcga ggaaaagtag tcccttctcg gcgattctgc    960
ggagggatct ccgtggggcg gtgaacgccg atgatgcctc tactaaccat gttcatgttt 1020 tcttttttt tctacaggtc ctgggtgacg aacag                             1055
```

Some embodiments of the present disclosure relate to the following nucleotide sequence SEQ ID No. 4 (a variable heavy-chain portion):

```
caggtacaac tgaaacaaag cgggcctggg ctggtccagc catcccaaag tttgtccata   60
acttgcactg ttagtggttt tagcttgacc aattacgggg tgcattgggt aagacagagt  120
cctggtaagg gcctcgaatg gctgggcgtg atatggtcag gcggcaatac tgactacaat  180
actccattta ccagcagatt gtccatcaat aaagataatt ctaaaagcca ggtattcttt  240
aagatgaact ctctgcagtc caatgatact gcaatttatt actgtgcccg agcacttacc  300
tactacgatt acgagttcgc atactggggc cagggtaccc tcgtgaccgt atctgcagcg  360
```

Some embodiments of the present disclosure relate to the following nucleotide sequence SEQ ID No. 5 (a variable light-chain portion):

```
gatatccttc tgactcaatc ccctgtgatt ctgtcagtgt caccagggga aagggtcagt   60
ttttcatgtc gcgcatctca aagcattggc actaacatcc actggtacca acaacgcaca  120
aacggaagtc cccgcttgct catcaagtat gcaagcgaat caatcagcgg gatcccttcc  180
aggttcagtg gtagtgggag tggtacagat ttcactctct caattaacag cgtagagtcc  240
gaggacatcg ccgactatta ttgccaacag aacaacaact ggcctactac atttggtgcc  300
ggtacaaaac tggagcttaa acgc                                        324
```

Some embodiments of the present disclosure relate to the following nucleotide sequence SEQ ID No. 6 (a human IgG-1 constant heavy-chain portion):

```
agcaccaagg gcccatcggt cttccccctg gcaccctcct ccaagagcac ctctggggc    60 acagcggccc tgggctgcct ggtcaaggac tacttccccg aaccggtgac ggtgtcgtgg  120
aactcaggcg ccctgaccag cggcgtgcac accttcccgg ctgtcctaca gtcctcagga  180
ctctactccc tcagcagcgt ggtgaccgtg ccctccagca gcttgggcac ccagacctac  240
atctgcaacg tgaatcacaa gcccagcaac accaaggtgg acaagaaagt tgagcccaaa  300
```

-continued

```
tcttgtgaca aaactcacac atgcccaccg tgcccagcac ctgaactcct gggggggaccg 360 tcagtcttcc tcttcccccc anaacccaag gacaccctca tgatctcccg gaccccctgag 420 gtcacatgcg tggtggtgga cgtgagccac gaagaccctg aggtcaagtt caactggtac 480
gtggacggcg tggaggtgca taatgccaag acaaagccgc gggaggagca gtacaacagc 540
acgtaccgtg tggtcagcgt cctcaccgtc ctgcaccagg actggctgaa tggcaaggag 600
tacaagtgca aggtctccaa caaagccctc ccagccccca tcgagaaaac catctccaaa 660
gccaaagggc agccccgaga accacaggtg tacaccctgc ccccatcccg ggaggagatg 720
accaagaacc aggtcagcct gacctgcctg gtcaaaggct tctatcccag cgacatcgcc 780
gtggagtggg agagcaatgg gcagccggag aacaactaca agaccacgcc tcccgtgctg 840
gactccgacg gctccttctt cctctacagc aagctcaccg tggacaagag caggtggcag 900
caggggaacg tcttctcatg ctccgtgatg catgaggctc tgcacaacca ctacacgcag 960
aagagcctct ccctgtctcc gggtaaa                                      987
```

Some embodiments of the present disclosure relate to the following nucleotide sequence SEQ ID No. 7 (a human IgG-1 Kappa light-chain portion):

```
ggtcagccca aggctgcccc ctcggtcact ctgttcccgc cctcctctga ggagcttcaa  60
gccaacaagg ccacactggt gtgtctcata agtgacttct acccgggagc cgtgacagtg 120
gcctggaagg cagatagcag ccccgtcaag gcgggagtgg agaccaccac acctccaaa  180 caaagcaaca caagtacgc ggccagcagc tatctgagcc tgacgcctga gcagtggaag 240
tcccacagaa gctacagctg ccaggtcacg catgaaggga gcaccgtgga aagacagtg 300 gcccctacag aatgttcata g                                            321
```

Some embodiments of the present disclosure relate to the following nucleotide sequence SEQ ID No. 8 (a Woodchuck Hepatitis Posttranslational Regulatory Element (WPRE) portion):

```
aatcaacctc tggattacaa aatttgtgaa agattgactg gtattcttaa ctatgttgct  60
ccttttacgc tatgtggata cgctgcttta atgcctttgt atcatgctat tgcttcccgt 120
atggctttca ttttctcctc cttgtataaa tcctggttgc tgtctcttta tgaggagttg 180
tggcccgrtg tcaggcaacg tggcgtggtg tgcactgtgt ttgctgacgc aaccccact  240 ggttggggca ttgccaccac ctgtcagctc ctttccggga ctttcgcttt ccccctccct 300
attgccacgg cggaactcat cgccgcctgc cttgcccgct gctggacagg ggctcggctg 360
ttgggcactg acaattccgt ggtgttgtcg gggaaatcat cgtcctttcc ttggctgctc 420
gcctgtgttg ccacctggat tctgcgcggg acgtccttct gctacgtccc ttcggccctc 480
aatccagcgg accttccttc ccgcggcctg ctgccggctc tgcggcctct tccgcgtctt 540
cgccttcgcc ctcagacgag tcggatctcc ctttgggccg cctccccgc              589
```

Some embodiments of the present disclosure relate to the following nucleotide sequence SEQ ID No. 9 (an AAV vector):

```
ctgcgcgctc gctcgctcac tgaggccgcc cgggcaaagc ccgggcgtcg ggcgaccttt  60
ggtcgcccgg cctcagtgag cgagcgagcg cgcagagagg gagtggccaa ctccatcact 120
```

-continued

```
aggggttcct tgtagttaat gattaacccg ccatgctact tatctacgta gccatgctct    180
aggacattga ttattgacta gtggagttcc gcgttacata acttacggta aatggcccgc    240
ctggctgacc gcccaacgac ccccgcccat tgacgtcaat aatgacgtat gttcccatag    300
taacgccaat agggactttc cattgacgtc aatgggtgga gtatttacgg taaactgccc    360
acttggcagt acatcaagtg tatcatatgc caagtacgcc ccctattgac gtcaatgacg    420
gtaaatggcc cgcctggcat tatgcccagt acatgacctt atgggacttt cctacttggc    480
agtacatcta cgtattagtc atcgctatta ccatggtcga ggtgagcccc acgttctgct    540
tcactctccc catctccccc ccctccccac cccaatttt gtatttattt atttttaat    600 tattttgtgc agcgatgggg gcggggggg ggggggcgc gcgccaggcg gggcggggcg    660
gggcgagggg cggggcgggg cgaggcgag aggtgcggcg gcagccaatc agagcggcgc    720
gctccgaaag tttcctttta tggcgaggcg gcggcggcgg cggccctata anaagcgaag    780
cgcgcggcgg gcgggagtcg ctgcgcgctg ccttcgcccc gtgccccgct ccgccgccgc    840
ctcgcgccgc ccgccccggc tctgactgac cgcgttacta aaacaggtaa gtccggcctc    900
cgcgccgggt tttggcgcct cccgcgggcg ccccctcct cacggcgagc gctgccacgt    960
cagacgaagg gcgcagcgag cgtcctgatc cttccgcccg gacgctcagg acagcggccc   1020
gctgctcata agactcggcc ttagaacccc agtatcagca aaggacatt ttaggacggg   1080 acttgggtga ctctagggca ctggtttct ttccagagag cggaacaggc gaggaaaagt   1140
agtcccttct cggcgattct gcggagggat ctccgtgggg cggtgaacgc cgatgatgcc   1200
tctactaacc atgttcatgt tttcttttt tttctacagg tcctgggtga cgaacagggt   1260
accgccacca tggcgacggg ttcaagaact tccctacttc ttgcatttgg cctgctttgt   1320
ttgccgtggt tacaggaggg ctcggcacag gtacaactga aacaaagcgg gcctgggctg   1380
gtccagccat cccaaagttt gtccataact tgcactgtta gtggttttag cttgaccaat   1440 tacgggtgc attgggtaag acagagtcct ggtaagggcc tcgaatggct gggcgtgata   1500
tggtcaggcg gcaatactga ctacaatact ccatttacca gcagattgtc catcaataaa   1560
gataattcta aaagccaggt attctttaag atgaactctc tgcagtccaa tgatactgca   1620
atttattact gtgcccgagc acttacctac tacgattacg agttcgcata ctggggccag   1680
ggtaccctcg tgaccgtatc tgcagcgagc accaagggcc catcggtctt ccccctggca   1740
ccctcctcca agagcacctc tgggggcaca gcggccctgg gctgcctggt caaggactac   1800
ttccccgaac cggtgacggt gtcgtggaac tcaggcgccc tgaccagcgg cgtgcacacc   1860
ttcccggctg tcctacagtc ctcaggactc tactccctca gcagcgtggt gaccgtgccc   1920
tccagcagct gggcaccca gacctacatc tgcaacgtga atcacaagcc cagcaacacc   1980
aaggtggaca agaaagttga gcccaaatct tgtgacaaaa ctcacacatg cccaccgtgc   2040
ccagcacctg aactcctggg gggaccgtca gtcttcctct tccccccaaa acccaaggac   2100
accctcatga tctcccggac ccctgaggtc acatgcgtgg tggtggacgt gagccacgaa   2160
gaccctgagg tcaagttcaa ctggtacgtg gacggcgtgg aggtgcataa tgccaagaca   2220
aagccgcggg aggagcagta caacagcacg taccgtgtgg tcagcgtcct caccgtcctg   2280
caccaggact ggctgaatgg caaggagtac aagtgcaagg tctccaacaa agccctccca   2340
gcccccatcg agaaaaccat ctccaaagcc aaagggcagc ccgagaacc acaggtgtac   2400 accctgcccc catcccggga ggagatgacc aagaaccagg tcagcctgac ctgcctggtc   2460
aaaggcttct atcccagcga catcgccgtg gagtgggaga gcaatgggca gccggagaac   2520
```

```
aactacaaga ccacgcctcc cgtgctggac tccgacggct ccttcttcct ctacagcaag    2580
ctcaccgtgg acaagagcag gtggcagcag gggaacgtct tctcatgctc cgtgatgcat    2640
gaggctctgc acaaccacta cacgcagaag agcctctccc tgtctccggg taaacgaaaa    2700
agaagatcag gttcgggtgc gccagtaaag cagacattaa actttgattt gctgaaactt    2760
gcaggtgatg tagagtcaaa tccaggtcca atggcaacag ggagccgaac ctctctgctc    2820
cttgctttcg ggctcctttg cctaccgtgg ctccaagagg gctcggcaga tatccttctg    2880
actcaatccc ctgtgattct gtcagtgtca ccaggggaaa gggtcagttt ttcatgtcgc    2940
gcatctcaaa gcattggcac taacatccac tggtaccaac aacgcacaaa cggaagtccc    3000
cgcttgctca tcaagtatgc aagcgaatca atcagcggga tcccttccag gttcagtggt    3060
agtgggagtg gtacagattt cactctctca attaacagcg tagagtccga ggacatcgcc    3120
gactattatt gccaacagaa caacaactgg cctactacat ttggtgccgg tacaaaactg    3180
gagcttaaac gcggtcagcc caaggctgcc ccctcggtca ctctgttccc gccctcctct    3240
gaggagcttc aagccaacaa ggccacactg gtgtgtctca taagtgactt ctacccggga    3300
gccgtgacag tggcctggaa ggcagatagc agccccgtca aggcgggagt ggagaccacc    3360
acaccctcca acaaagcaa caacaagtac gcggccagca gctatctgag cctgacgcct    3420
gagcagtgga agtcccacag aagctacagc tgccaggtca cgcatgaagg gagcaccgtg    3480
gagaagacag tggcccctac agaatgttca tagtctagaa taatcaacct ctggattaca    3540
aaatttgtga agattgact ggtattctta actatgttgc tccttttacg ctatgtggat    3600
acgctgcttt aatgcctttg tatcatgcta ttgcttcccg tatggctttc attttctcct    3660
ccttgtataa atcctggttg ctgtctcttt atgaggagtt gtggcccgtt gtcaggcaac    3720
gtggcgtggt gtgcactgtg tttgctgacg caacccccac tggttggggc attgccacca    3780
cctgtcagct ccttccggg actttcgctt tcccctccc tattgccacg cggaactca    3840 tcgccgcctg ccttgcccgc tgctggacag gggctcggct gttgggcact gacaattccg    3900
tggtgttgtc ggggaaatca tcgtcctttc cttggctgct cgcctgtgtt gccacctgga    3960
ttctgcgcgg gacgtccttc tgctacgtcc cttcggccct caatccagcg gaccttcctt    4020
cccgcggcct gctgccggct ctgcggcctc ttccgcgtct tcgccttcgc cctcagacga    4080
gtcggatctc cctttgggcc gcctccccgc ctaagcttat cgataccgtc gagatctaac    4140
ttgtttattg cagcttataa tggttacaaa taaagcaata gcatcacaaa tttcacaaat    4200
aaagcatttt tttcactgca ttctagttgt ggtttgtcca aactcatcaa tgtatcttat    4260
catgtctgga tctcgacctc gactagagca tggctacgta gataagtagc atggcgggtt    4320
aatcattaac tacaaggaac ccctagtgat ggagttggcc actccctctc tgcgcgctcg    4380
ctcgctcact gaggccgggc gaccaaaggt cgcccgacgc ccgggctttg cccggcggc    4440 ctcagtgagc gagcgagcgc gccagctggc gtaatagcga agaggcccgc accgatcgcc    4500
cttcccaaca gttgcgcagc ctgaatggcg aatggaattc cagacgattg agcgtcaaaa    4560
tgtaggtatt tccatgagcg ttttcctgt tgcaatggct ggcggtaata ttgttctgga    4620
tattaccagc aaggccgata gtttgagttc ttctactcag gcaagtgatg ttattactaa    4680
tcaaagaagt attgcgacaa cggttaattt gcgtgatgga cagactcttt tactcggtgg    4740
cctcactgat tataaaaaca cttctcagga ttctggcgta ccgttcctgt ctaaaatccc    4800
tttaatcggc ctcctgttta gctcccgctc tgattctaac gaggaaagca cgttatacgt    4860
gctcgtcaaa gcaaccatag tacgcgcccct gtagcggcgc attaagcgcg gcgggtgtgg    4920
tggttacgcg cagcgtgacc gctacacttg ccagcgccct agcgcccgct cctttcgctt    4980
```

```
tcttcccttc ctttctcgcc acgttcgccg gctttccccg tcaagctcta aatcggggc    5040
tcccttttagg gttccgattt agtgctttac ggcacctcga ccccaaaaaa cttgattagg   5100
gtgatggttc acgtagtggg ccatcgccct gatagacggt ttttcgccct ttgacgttgg   5160
agtccacgtt ctttaatagt ggactcttgt tccaaactgg aacaacactc aaccctatct   5220
cggtctattc ttttgattta taagggattt tgccgatttc ggcctattgg ttaaaaaatg   5280
agctgattta acaaaaattt aacgcgaatt ttaacaaaat attaacgttt acaatttaaa   5340
tatttgctta tacaatcttc ctgttttggg gcttttctg attatcaacc ggggtacata    5400
tgattgacat gctagtttta cgattaccgt tcatcgattc tcttgtttgc tccagactct   5460
caggcaatga cctgatagcc tttgtagaga cctctcaaaa atagctaccc tctccggcat   5520
gaatttatca gctagaacgg ttgaatatca tattgatggt gatttgactg tctccggcct   5580
ttctcacccg tttgaatctt tacctacaca ttactcaggc attgcattta aaatatatga   5640
gggttctaaa aatttttatc cttgcgttga aataaaggct tctcccgcaa agtattaca    5700
gggtcataat gttttggta caaccgattt agctttatgc tctgaggctt tattgcttaa    5760
ttttgctaat tctttgcctt gcctgtatga tttattggat gttggaattc ctgatgcggt   5820
attttctcct tacgcatctg tgcggtattt cacaccgcat atggtgcact ctcagtacaa   5880
tctgctctga tgccgcatag ttaagccagc cccgacaccc gccaacaccc gctgacgcgc   5940
cctgacgggc ttgtctgctc ccggcatccg cttacagaca agctgtgacc gtctccggga   6000
gctgcatgtg tcagaggttt tcaccgtcat caccgaaacg cgcgagacga agggcctcg    6060
tgatacgcct attttatag gttaatgtca tgataataat ggtttcttag acgtcaggtg    6120
gcacttttcg gggaaatgtg cgcggaaccc ctatttgttt attttctaa atacattcaa    6180
atatgtatcc gctcatgaga caataaccct gataaatgct tcaataatat tgaaaagga    6240
agagtatgag tattcaacat ttccgtgtcg cccttattcc cttttttgcg gcattttgcc   6300
ttcctgtttt tgctcaccca gaaacgctgg tgaaagtaaa agatgctgaa gatcagttgg   6360
gtgcacgagt gggttacatc gaactggatc tcaacagcgg taagatcctt gagagttttc   6420
gccccgaaga acgttttcca atgatgagca cttttaaagt tctgctatgt ggcgcggtat   6480
tatcccgtat tgacgccggg caagagcaac tcggtcgccg catacactat tctcagaatg   6540
acttggttga gtactcacca gtcacagaaa agcatcttac ggatggcatg acagtaagag   6600
aattatgcag tgctgccata accatgagtg ataacactgc ggccaactta cttctgacaa   6660
cgatcggagg accgaaggag ctaaccgctt ttttgcacaa catgggggat catgtaactc   6720
gccttgatcg ttgggaaccg gagctgaatg aagccatacc aaacgacgag cgtgacacca   6780
cgatgcctgt agcaatggca acaacgttgc gcaaactatt aactggcgaa ctacttactc   6840
tagcttcccg gcaacaatta atagactgga tggaggcgga taaagttgca ggaccacttc   6900
tgcgctcggc ccttccggct ggctggttta ttgctgataa atctggagcc ggtgagcgtg   6960
ggtctcgcgg tatcattgca gcactggggc cagatggtaa gccctcccgt atcgtagtta   7020
tctacacgac ggggagtcag gcaactatgg atgaacgaaa tagacagatc gctgagatag   7080
gtgcctcact gattaagcat tggtaactgt cagaccaagt ttactcatat atactttaga   7140
ttgatttaaa acttcatttt taatttaaaa ggatctaggt gaagatcctt tttgataatc   7200
tcatgaccaa aatcccttaa cgtgagtttt cgttccactg agcgtcagac cccgtagaaa   7260
agatcaaagg atcttcttga gatccttttt ttctgcgcgt aatctgctgc ttgcaaacaa   7320
aaaaaccacc gctaccagcg gtggtttgtt tgccggatca agagctacca actcttttc    7380
```

-continued

```
cgaaggtaac tggcttcagc agagcgcaga taccaaatac tgtccttcta gtgtagccgt    7440
agttaggcca ccacttcaag aactctgtag caccgcctac atacctcgct ctgctaatcc    7500
tgttaccagt ggctgctgcc agtggcgata agtcgtgtct taccgggttg gactcaagac    7560
gatagttacc ggataaggcg cagcggtcgg gctgaacggg gggttcgtgc acacagccca    7620
gcttggagcg aacgacctac accgaactga gatacctaca gcgtgagcta tgagaaagcg    7680
ccacgcttcc cgaagggaga aaggcggaca ggtatccggt aagcggcagg gtcggaacag    7740
gagagcgcac gagggagctt ccaggggaa acgcctggta tctttatagt cctgtcgggt     7800
ttcgccacct ctgacttgag cgtcgatttt tgtgatgctc gtcaggggg cggagcctat     7860 ggaaaaacgc cagcaacgcg gcctttttac ggttcctggc cttttgctgg ccttttgctc    7920
acatgttctt tcctgcgtta tcccctgatt ctgtggataa ccgtattacc gcctttgagt    7980
gagctgatac cgctcgccgc agccgaacga ccgagcgcag cgagtcagtg agcgaggaag    8040
cggaagagcg cccaatacgc aaaccgcctc tccccgcgcg ttggccgatt cattaatgca    8100
gcag                                                                 8104
```

Some embodiments of the present disclosure relate to the insert that comprises the nucleotide sequences: SEQ ID No. 1, SEQ ID No. 2. SEQ ID No. 3, SEQ ID No. 4, SEQ ID No. 5, SEQ ID No. 6, SEQ ID No. 7, SEQ ID No. 8 or combinations thereof. Some embodiments of the present disclosure relate to the insert that comprises the nucleotide sequences: SEQ ID No. 4 and SEQ ID No. 7.

Some embodiments of the present disclosure relate to a composition of matter and/or the agent that comprises the nucleotide sequence of SEQ ID No. 9.

The nucleotide sequence encoding the CLP or a sub-peptide thereof may be linked directly or indirectly to the nucleotide sequence encoding the immunoglobulin. By "directly", it is meant that the sequences are continuous without intervening nucleotides. By "indirectly", it is meant that there are intervening nucleotides. The intervening nucleotides may, for example, be a linker peptide and/or a hinge peptide. In an embodiment, there are nucleotides encoding a flexible linker peptide and a hinge peptide positioned between nucleotide sequence encoding the CLP or sub-peptide thereof and the nucleotide sequence encoding the immunoglobulin.

Example 1—Expression Cassette

Expression cassettes for expressing the CLP in a subject cell were synthesized by Genscript. Each cassette contained a signal peptide, the precursor protein that may be followed by a self-cleaving 2A peptide sequence, a signal peptide and the human lambda constant domain. The synthesized CLP expression cassettes were cloned into the pAVA-00200 plasmid backbone containing the CASI promoter1, multiple cloning site (MCS), Woodchuck Hepatitis Virus post-transcriptional regulatory element (WPRE), Simian virus 40 (SV40) polyadenylation (polyA) sequence all flanked by the AAV2 inverted terminal repeats (ITR), pAVA-00200 was cut with the restriction enzymes KpnI and XbaI in the MCS and separated on a 1% agarose gel. The band of interest was excised and purified using a gel extraction kit. Each CLP expression cassette was amplified by PCR using Taq polymerase and the PCR products were gel purified and the bands on interest were also excised and purified using a gel extraction kit. These PCR products contained the CLP expression cassettes in addition to 15 base pair 5' and 3' overhangs that align with the ends of the linearized pAVA-00200 backbone. Using in-fusion cloning2, the amplified CLP expression cassettes are integrated with the pAVA-00200 backbone via homologous recombination. The resulting plasmid vectors contained at least the following: 5' ITR, a CASI promoter, the CLP expression cassette. WPRE, and a 3' ITR, per SEQ ID No. 9.

Example 2—Experimental Data

The ovarian bursa of C57BL/6 mice were implanted with $1 \times 10^6$ ID8 epithelial carcinoma cells. About 60 days later, eight mice were administered i.p. 50 mM phosphate buffered saline (control group) or $1 \times 10^{10}$ vg of the AAV comprising SEQ ID No. 9 (treatment group).

The serum samples were analyzed using a quantitative ELISA to measure human IgG-1 levels (as an indicator of CLP production). The analysis of the serum samples from the animals in the control group showed that no human IgG-1 was detected. FIG. 1 shows experimental human IgG CLP expression data, as an indirect measure of CLP expression obtained from the treatment group. Without being bound by any particular theory, the mice in the treatment group expressed CLP up to 28 days following administration of the AAV vector that comprised the SEQ ID No. 9.

The invention claimed is:

1. A composition that comprises a nucleotide sequence according to SEQ ID No. 9 that can be expressed in a target cell.

2. A pharmaceutical composition comprising a nucleotide sequence according to SEQ ID No. 9 and one or more pharmaceutically acceptable carriers and/or one or more excipients.

3. A method of making an agent/target cell complex, the method comprising a step of administering a nucleotide sequence according to SEQ ID No. 9 to a target cell for forming the agent/target cell complex, wherein the agent/target cell complex causes the target cell to increase production of a Cetuximab-like protein (CLP).

4. The method of claim 3, wherein the target cell is one or more of an adrenal gland cell; a bile duct cell; a chondrocyte; a cochlear cell; a corneal cell; an endocardium cell; an endometrial cell; an endothelial cell; an epithelial cell; a fibroblast; a hair follicle cell; a hepatocyte; a lymph node cell; a mucosal cell; a myocyte; a neuron; a glomeruli cell; an optic nerve cell; an osteoblast; an ovarian tissue cell; a pancreatic islet beta cell; a pericardium cell; a platelet; a red blood cell (RBC); a retinal cell; a scleral cell; a Schwann cell; a T cell; a testicular tissue cell; a thyroid gland cell; a uveal cell; a